US011147534B2

(12) United States Patent
Arai et al.

(10) Patent No.: US 11,147,534 B2
(45) Date of Patent: Oct. 19, 2021

(54) PROBE ADAPTER, ULTRASONIC IMAGING APPARATUS, ULTRASONIC IMAGING METHOD AND ULTRASONIC IMAGING PROGRAM

(71) Applicant: FURUNO ELECTRIC CO., LTD., Nishinomiya (JP)

(72) Inventors: Tatsuo Arai, Takarazuka (JP); Satoshi Nakamura, Kobe (JP); Takeshi Kawajiri, Takarazuka (JP)

(73) Assignee: Furuno Electric Co., Ltd., Nishinomiya (JP)

(*) Notice: Subject to any disclaimer, the term of this patent is extended or adjusted under 35 U.S.C. 154(b) by 472 days.

(21) Appl. No.: 15/744,729

(22) PCT Filed: Jun. 7, 2016

(86) PCT No.: PCT/JP2016/066819
§ 371 (c)(1),
(2) Date: Jan. 12, 2018

(87) PCT Pub. No.: WO2017/010193
PCT Pub. Date: Jan. 19, 2017

(65) Prior Publication Data
US 2018/0263596 A1      Sep. 20, 2018

(30) Foreign Application Priority Data

Jul. 13, 2015   (JP) .............................. JP2015-139908

(51) Int. Cl.
*A61B 8/00* (2006.01)
*A61B 8/14* (2006.01)
*A61B 8/08* (2006.01)

(52) U.S. Cl.
CPC .............. *A61B 8/4209* (2013.01); *A61B 8/14* (2013.01); *A61B 8/4281* (2013.01);
(Continued)

(58) Field of Classification Search
CPC combination set(s) only.
See application file for complete search history.

(56) References Cited

U.S. PATENT DOCUMENTS 4,431,007 A * 2/1984 Amazeen ................. A61B 8/08
600/440
4,920,966 A * 5/1990 Hon ...................... A61B 5/4356
600/459
(Continued)

FOREIGN PATENT DOCUMENTS

CN       101106944        1/2008
CN       101106944 A      1/2008
(Continued)

OTHER PUBLICATIONS

International Search Report in PCT Application No. PCT/JP2016/066819 dated Jul. 28, 2016, dated Aug. 9, 2016 in 5 pages.
(Continued)

*Primary Examiner* — Oommen Jacob
(74) *Attorney, Agent, or Firm* — Knobbe Martens Olson & Bear, LLP

(57) ABSTRACT

Provided is an art in which when an operator grips a probe of an ultrasonic imaging apparatus and moves the probe, it is facilitated to maintain the probe at a suitable angle with respect to an object to be imaged. A probe adapter may include a contact surface having a shape extending along an outer circumference of a cross section of an object to be imaged, and a fixing portion configured to fix a probe having an ultrasonic wave transmitting-receiving surface which transmits and receives an ultrasonic wave at a given angle and expose the ultrasonic wave transmitting-receiving surface to the contact surface side.

18 Claims, 11 Drawing Sheets

(52) U.S. Cl.
CPC .......... *A61B 8/4444* (2013.01); *A61B 8/5207* (2013.01); *A61B 8/5253* (2013.01)

(56) References Cited

U.S. PATENT DOCUMENTS

| | | | | |
|---|---|---|---|---|
| 5,394,877 | A * | 3/1995 | Orr ...................... | A61B 5/0408 |
| | | | | 600/459 |
| RE34,964 | E * | 6/1995 | Okazaki .................. | A61B 8/14 |
| | | | | 600/439 |
| 5,913,243 | A | 6/1999 | Hopeck et al. | |
| 6,048,323 | A * | 4/2000 | Hon ...................... | A61B 5/4356 |
| | | | | 600/588 |
| 6,511,427 | B1 * | 1/2003 | Sliwa, Jr. ............. | A61B 5/4869 |
| | | | | 600/438 |
| 7,029,446 | B2 | 4/2006 | Wendelken et al. | |
| 7,914,456 | B2 * | 3/2011 | Osaka .................. | A61B 5/0048 |
| | | | | 600/447 |
| 9,615,815 | B2 * | 4/2017 | Kwartowitz ......... | A61B 8/5223 |
| 2002/0167533 | A1 * | 11/2002 | Tirumalai ........... | G01S 15/8995 |
| | | | | 345/629 |
| 2004/0087851 | A1 * | 5/2004 | Lee ...................... | A61B 8/4209 |
| | | | | 600/407 |
| 2004/0122319 | A1 * | 6/2004 | Mehi .................... | A61B 8/4483 |
| | | | | 600/443 |
| 2005/0165310 | A1 * | 7/2005 | Bindefeld ............ | A61B 8/4472 |
| | | | | 600/453 |
| 2007/0055159 | A1 * | 3/2007 | Wang .................. | A61B 8/4281 |
| | | | | 600/443 |
| 2009/0177083 | A1 | 7/2009 | Matsumura | |
| 2009/0275833 | A1 | 11/2009 | Ikeda et al. | |
| 2009/0306502 | A1 * | 12/2009 | Lacoste ................ | A61B 8/4281 |
| | | | | 600/439 |
| 2010/0174185 | A1 * | 7/2010 | Wang ................... | A61B 8/14 |
| | | | | 600/437 |
| 2011/0196238 | A1 * | 8/2011 | Jacobson ............. | A61B 8/4281 |
| | | | | 600/459 |
| 2012/0232401 | A1 | 9/2012 | Takagi et al. | |
| 2013/0150725 | A1 | 6/2013 | Choi | |
| 2014/0058265 | A1 * | 2/2014 | Wang .................. | A61B 8/4461 |
| | | | | 600/447 |
| 2015/0209016 | A1 * | 7/2015 | Lefebvre ............. | G01S 15/8936 |
| | | | | 600/472 |
| 2018/0263596 | A1 * | 9/2018 | Arai ..................... | A61B 8/4281 |

FOREIGN PATENT DOCUMENTS

| | | |
|---|---|---|
| CN | 101193594 | 6/2008 |
| CN | 101329306 A | 12/2008 |
| CN | 201662564 U | 12/2010 |
| CN | 103156641 | 6/2013 |
| CN | 104068890 A | 10/2014 |
| JP | A1984-111744 | 6/1984 |
| JP | 2001-087267 A | 4/2001 |
| JP | 2004-229958 A | 8/2004 |
| JP | 2005-137581 A | 6/2005 |
| JP | 2008073391 | 4/2008 |
| JP | 2008-284136 A | 11/2008 |
| JP | 2011-217927 A | 11/2011 |
| JP | 2012-029718 A | 2/2012 |
| KR | 20070006311 | 1/2007 |

OTHER PUBLICATIONS

T. Fukunaga, "Calculation of Muscle Strength per Unit Cross-Sectional Area of Human Muscle by Means of Ultrasonic Measurement" J-STAGE vol. 14 (1969) Issue 1 pp. 28-32.

European Search Report for Application No. 16 82 4173, dated Feb. 27, 2019 in 29 pages.

* cited by examiner (A)

(B)

(A)

(B)

(A)

(B)

PROBE ADAPTER, ULTRASONIC IMAGING APPARATUS, ULTRASONIC IMAGING METHOD AND ULTRASONIC IMAGING PROGRAM

CROSS REFERENCE TO RELATED APPLICATIONS

This application claims priority under 35 U.S.C. § 119 to Japanese Patent Application No. 2015-139908, which was filed on Jul. 13, 2015, the entire disclosure of which is hereby incorporated by reference.

TECHNICAL FIELD

The present disclosure relates to an art in which cross sections of a thigh, an upper arm, an abdomen etc. of a human body are imaged by using a probe which transmits and receives ultrasonic waves.

BACKGROUND

Quadricepses are thigh muscles which control movements for raising a thigh, straightening a knee joint, etc. A muscle mass of the quadriceps significantly decreases due to aging, which becomes a factor of a walking difficulty and falling of elderly people. Therefore, the muscle mass etc. of the quadriceps need to be grasped when providing a medical aid for the walking difficulty and falling of the elderly people. For this reason, an entire cross section of the thigh is conventionally imaged using a CT (Computed Tomography) device or an MRI (Magnetic Resonance Imaging) device.

However, the CT device and the MRI device are expensive and take long time to image, therefore, a simpler art for imaging is desired. Thus, various arts for imaging a wide range of a cross section of a human body by using ultrasonic waves and arts for measuring a muscle mass by using ultrasonic waves are devised (e.g., see Patent Documents 1 to 3 and Non-Patent Document 1).

An ultrasonic imaging apparatus disclosed in Patent Document 1 includes a plurality of probes arranged along a circumferential surface of a thigh and for generating a plurality of fragment images obtained by imaging the vicinity of the probes. Further, by composing the plurality of generated fragment images, an image in which a wide range of a cross section of a human body is captured is generated.

An ultrasonic imaging apparatus disclosed in Patent Document 2 includes a water tank into which a thigh is placed, a single probe provided along an outer circumferential surface of the water tank, and a motor for moving the probe along the outer circumferential surface of the water tank. The ultrasonic imaging apparatus generates a plurality of fragment images while moving the probe. Further, by composing the plurality of generated fragment images, an image in which a wide range of a cross section of a human body is captured is generated.

REFERENCE DOCUMENTS OF CONVENTIONAL ART

Patent Documents

[Patent Document 1] JP2005-137581A
[Patent Document 2] JP2001-087267A
[Patent Document 2] JPH03-029111U
[Non-Patent Document]

[Non-Patent Document 1] Tetsuo Fukunaga, "Calculation of Muscle Strength per Unit Cross-Sectional Area of Human Muscle by Means of Sonic Measurement" in 1969 by Japan Journal of Physical Education, Health and Sport Sciences

DESCRIPTION OF THE DISCLOSURE

Problems to be Solved by the Disclosure

The conventional ultrasonic imaging apparatuses disclosed in Patent Documents 1 and 2 have complex configurations and are large in scale, and require time and labor for attaching the probe(s). Therefore, imaging the cross section of the human body takes relatively long time.

It may also be considered to use an ultrasonic imaging apparatus having a general configuration so that a wide range of a cross section of a human body is imaged by an operator gripping and moving a probe. Here, in order to image the wide range of the cross section of the human body in this manner, the operator needs to move the probe along the cross section to be imaged, while maintaining the probe at a suitable angle with respect to a surface of the human body. However, it is not easy for the operator to keep maintaining the suitable angle while moving the probe.

Generally, it is effective to use a probe having a wide tip end surface which comes in contact with the surface of the human body in order to image an area as wide as possible in single imaging. However, in a case where the subject part is a curved surface, since an edge portion of the wide tip end surface of the probe becomes easier to separate from the surface of the human body, it is necessary to strongly press the tip end surface of the probe against the surface of the human body. In this case, the surface and internal tissues of the human body are deformed, and therefore, it becomes difficult to accurately image the shapes of the internal tissues.

Therefore, the purpose of the present disclosure is to provide an art in which, when an operator grips a probe of an ultrasonic imaging apparatus and moves the probe, it is facilitated to maintain the probe at a suitable angle with respect to an object to be imaged, without strongly pressing the probe against the object to be imaged.

SUMMARY OF THE DISCLOSURE

According to one aspect of the present disclosure, a probe adapter may include a contact surface configured to have a shape extending along an outer circumference of a cross section of an object to be imaged. The probe adapter may fix a probe having an ultrasonic wave transmitting-receiving surface at a given angle and expose the ultrasonic wave transmitting-receiving surface to the contact surface side.

By attaching this probe adapter to the probe, even when moving the probe along a surface of the object to be imaged while being in contact with the object to be imaged having a curved surface like a thigh, a large contact area between the probe and the object to be imaged may be maintained by the probe adapter. Thus, it may become easy to use a probe which is thin such that the entire surface of the ultrasonic wave transmitting-receiving surface contacts the surface of the object to be imaged, and move it while keeping the angle thereof with respect to the surface of the object to be imaged constant. Therefore, without strongly pressing the probe against the object to be imaged, a shape of an internal tissue of the object to be imaged may accurately be imaged.

Further, according to another aspect of the present disclosure, an ultrasonic imaging apparatus may include the probe adapter and the probe described above or a prove having a contact surface which is equivalent to that of the prove adapter. The ultrasonic imaging apparatus may repeatedly transmit from the probe an ultrasonic wave into an object to be imaged and receive by the probe the ultrasonic wave reflected inside the object to be imaged every time the ultrasonic wave is transmitted. The ultrasonic imaging apparatus may generate a fragment image in which the object to be imaged is internally partially captured based on the received ultrasonic wave. The ultrasonic imaging apparatus may compose a plurality of fragment images generated by a fragment image generating module. Here, the fragment images may be an image captured in single imaging in a linear scan mode or a sector scan mode and equivalent to an image captured by an ultrasonic diagnosis apparatus with a general configuration (ultrasonic imaging apparatus).

With this configuration, since the angle of the probe is easily stabilized when an operator moves the probe, the inside of the object to be imaged may be captured from various directions under a constant angle condition. Thus, the plurality of fragment images in which the inside of the object to be imaged are vividly captured from various directions may be generated. Further, by composing such fragment images, the inside of the object to be imaged may be captured vividly and over a wide range.

Further, the ultrasonic imaging apparatus may repeatedly switch an operation state of the probe between a state where the probe is operated in a linear scan mode in which a range extending in a belt shape from the ultrasonic wave transmitting-receiving surface is imaged, and a state where the probe is operated in a sector scan mode in which a range spreading in a fan shape from the ultrasonic wave transmitting-receiving surface is imaged.

In the linear scan mode, the range extending in the belt shape from the ultrasonic wave transmitting-receiving surface may be imaged vividly. However, if a contour portion of the internal tissue of the object to be imaged extends perpendicular to the surface of the object to be imaged, it may be difficult to image the contour portion vividly in the linear scan mode. On the other hand, in the sector scan mode, since a wider angle range than the range extending in the belt shape from the ultrasonic wave transmitting-receiving surface may be imaged, the contour portion extending perpendicular to the surface of the object to be imaged in the internal tissue may be imaged. Therefore, by composing the fragment image obtained in the linear scan mode and the fragment image obtained in the sector scan mode, the image in which the vicinity of the probe is imaged vividly and the contour portion perpendicularly to the surface of the internal tissue is also imaged may be obtained.

The ultrasonic imaging apparatus may further include an angle sensor configured to detect a direction in which the ultrasonic wave transmitting-receiving surface faces. The plurality of fragment images may be composed based on the angle detected by the angle sensor.

With this configuration, the plurality of fragment images may suitably be composed and the inside of the object to be imaged may be captured more accurately.

According to the present disclosure, when an operator grips a probe of an ultrasonic imaging apparatus and moves the probe, it is facilitated to maintain the probe at a suitable angle with respect to an object to be imaged, without strongly pressing the probe against the object to be imaged.

DETAILED DESCRIPTION

Hereinafter, an ultrasonic imaging apparatus, an ultrasonic imaging method, and an ultrasonic imaging program according to some embodiments of the present disclosure are described with reference to the accompanying drawings.

Figure 1:
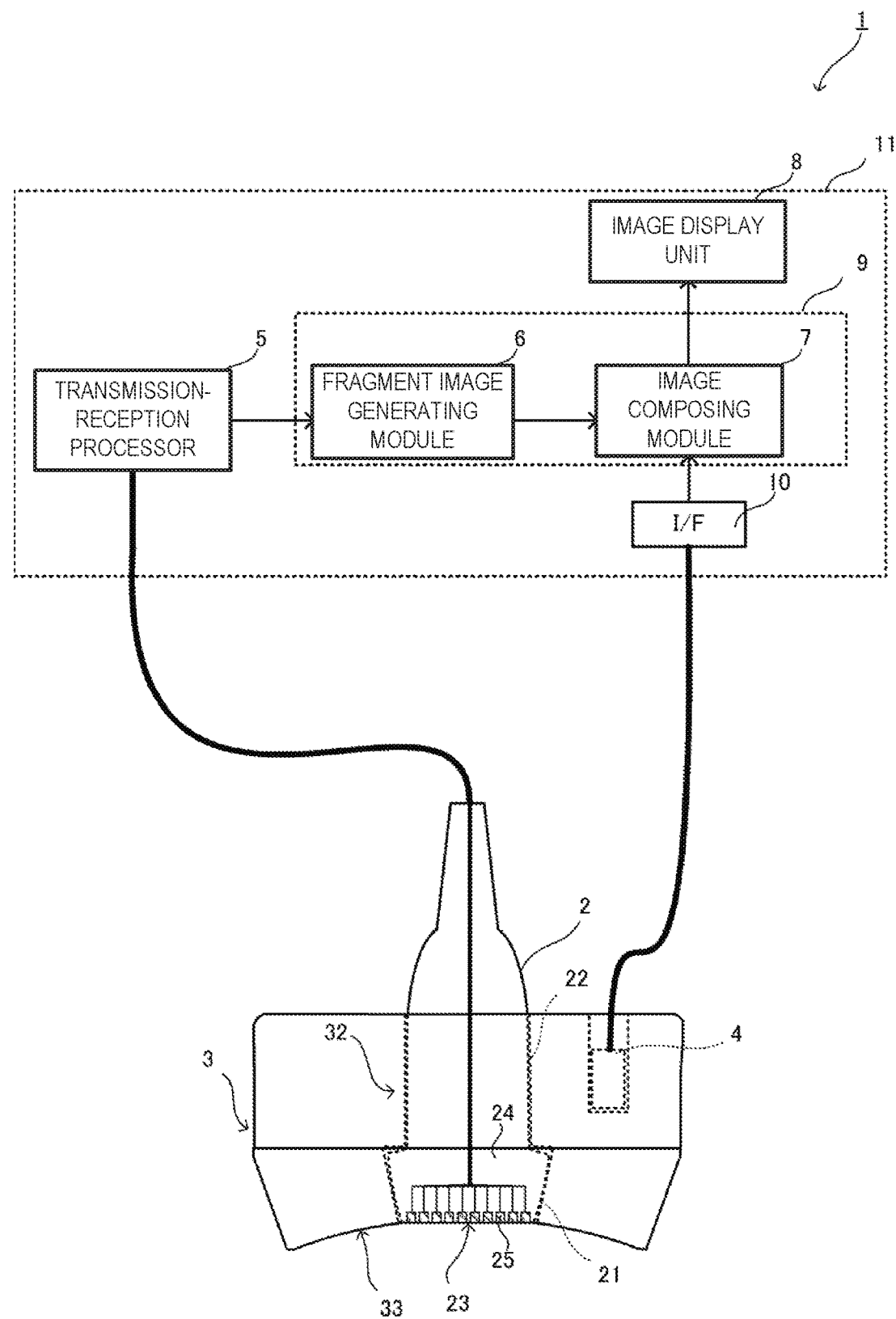
FIG. 1 is a configuration diagram of an ultrasonic imaging apparatus according to one embodiment of the present disclosure.

FIG. 1 is a configuration diagram of the ultrasonic imaging apparatus according to one embodiment of the present disclosure. The ultrasonic imaging apparatus 1 may include a probe 2, a probe adapter 3, an angle sensor 4, and an image processing device 11.

The probe 2 may have a substantially pillar shape and be configured so that an operator can grip and move it. The probe 2 may include an ultrasonic wave transmitting-receiving surface 23. The ultrasonic wave transmitting-receiving surface 23 may be provided on a lower end surface of the probe 2. The probe 2 may be connected to a transmission-reception processor 5 of the image processing device 11 via a cable which is connected to an upper end of the probe 2. The probe 2, upon receiving a transmission signal from the image processing device 11, may transmit an ultrasonic wave from the ultrasonic wave transmitting-receiving surface 23, receive an ultrasonic wave by the ultrasonic wave transmitting-receiving surface 23, and output a reception signal corresponding to a reception level of the ultrasonic wave to the image processing device 11.

More particularly, the probe 2 may include a tip end part 21 and a grip part 22. The ultrasonic wave transmitting-receiving surface 23 may be provided on a lower surface of the tip end part 21. Note that the probe 2 may have a different shape from that illustrated in FIG. 1.

Further, for example, the ultrasonic wave transmitting-receiving surface 23 may be formed so that a plurality of ultrasonic oscillators 25 are structured into a single-dimensionally arranged array type. Each ultrasonic oscillator 25 may be connected to the transmission-reception processor 5 of the image processing device 11 via the cable. The transmission-reception processor 5 may control a phase difference between signals which are inputted and outputted into and from the adjacent ultrasonic oscillators 25, to adjust a beam shape of the ultrasonic waves transmitted and received by the ultrasonic wave transmitting-receiving surface 23. Note that, the ultrasonic wave transmitting-receiving surface 23 may be structured into a single element type which only includes a single ultrasonic oscillator. In this case, the beam shape of the ultrasonic waves which are transmitted and received by the ultrasonic wave transmitting-receiving surface 23 may uniquely be defined.

The angle sensor 4 may be attached to the probe adapter 3 together with the probe 2 and detect a tilt of the probe 2 with respect to a vertical direction. The angle sensor 4 may be connected to an interface 10 of the image processing device 11 via a cable connected to an upper end of the angle sensor 4. Note that the angle sensor 4 may not necessarily be provided.

The probe adapter 3 may substantially have a size which fits into a hand and be attached to surround a lower end side of the probe 2. The probe adapter 3 may include a contact surface 33 and a fixing portion 32. The contact surface 33 may have a shape extending along an outer circumference of a cross section of an object to be imaged, such as a thigh. The fixing portion 32 may fix the probe 2 at a given angle and expose the ultrasonic wave transmitting-receiving surface 23 of the probe 2 to the contact surface 33 side.

Since the probe adapter 3 may have the contact surface 33 as described above, when moving the probe 2 along a surface of the object to be imaged, a large contact area with the object to be imaged may be maintained by the probe adapter 3. Therefore, even if the ultrasonic wave transmitting-receiving surface 23 of the probe 2 is thin, it may become easy to move the probe 2 while keeping the angle of the probe 2 with respect to the surface of the object to be imaged constant.

Figure 2:
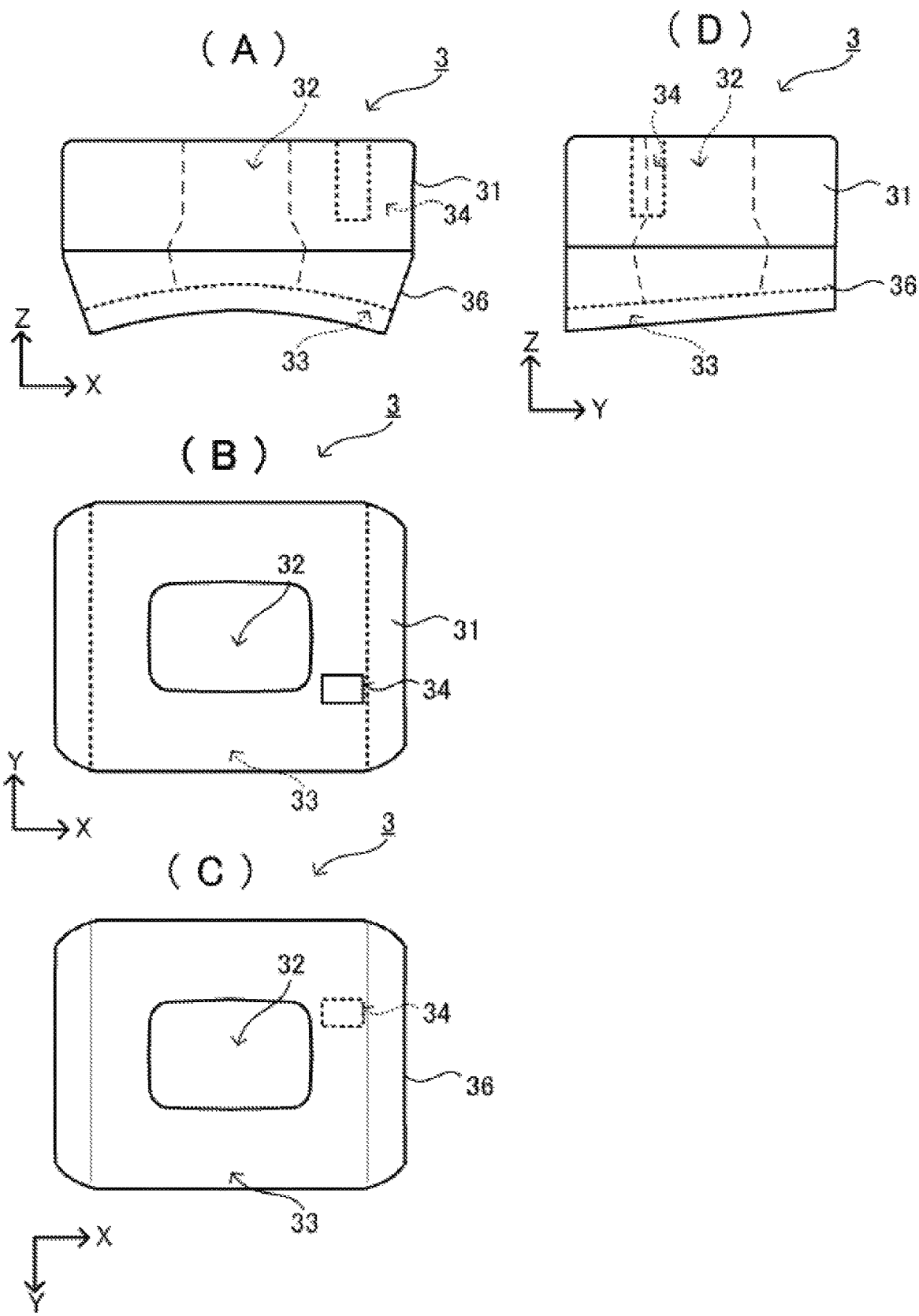
FIGS. 2(A) to 2(D) are exploded views of a probe adapter according to the embodiment of the present disclosure.

Further, the probe adapter 3 may have a structure illustrated in FIGS. 2(A) to 2(D). FIG. 2(A) is a front elevational view of the probe adapter 3. FIG. 2(B) is a top plan view of the probe adapter 3. FIG. 2(C) is a bottom plan view of the probe adapter 3. FIG. 2(D) is a right-side view of the probe adapter 3.

The probe adapter 3 may include a housing 31. The housing 31 may be a member constituting an upper surface part of the probe adapter 3. The probe adapter 3 may also have an accommodating section 34. The accommodating section 34 may be a rectangular-cylindrical concave formed to open to an upper surface of the housing 31 and accommodate the angle sensor 4.

The fixing portion 32 may be formed by a through-hole perpendicularly extending from the upper surface of the probe adapter 3 and fix the probe 2 by coming into contact with the grip part 22 inside the through-hole.

Further, the probe adapter 3 may also include a detachable-attaching part 36 which is detachable from the housing 31. The detachable-attaching part 36 may be a member constituting a lower surface part of the probe adapter 3. The detachable-attaching part 36 may be structured to be detachable from the probe adapter 3 by using a magnet, etc. A lower surface of the detachable-attaching part 36 may be structured as the contact surface 33. The contact surface 33 may be concaved into a groove shape and have a shape substantially matching with a surface of the imaging target which bulges like a thigh. Further, as illustrated in FIG. 2(D), the detachable-attaching part 36 may be structured to be gradually thinner from the front side to the rear side. Therefore, the contact surface 33 may extend in a direction tilted from the upper surface of the probe adapter 3. Since the probe 2 may be fixed perpendicularly to the upper surface of the probe adapter 3 as described above, the contact surface 33 may not be perpendicular to the probe 2.

Thus, by structuring the detachable-attaching part 36 to be detachable from the probe adapter 3, the detachable-attaching part 36 may be replaced with another one having a different shape, or the detachable-attaching part 36 may be attached by switching the front side and the rear side with each other. Therefore, by preparing a plurality of detachable-attaching parts 36 having different curvatures, inclinations etc. at the contact surface 33, the detachable-attaching part 36 corresponding to the shape of the object to be imaged may be attached to the probe adapter 3.

Figure 3:
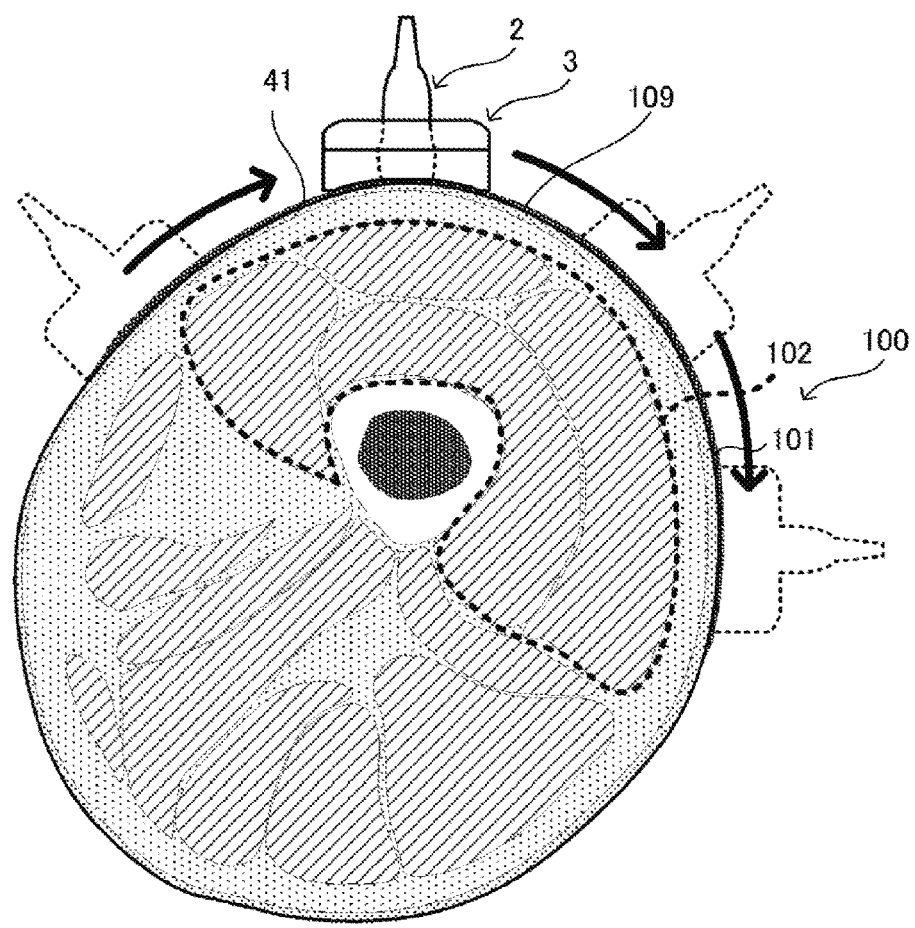
FIGS. 3(A) and 3(B) are views illustrating an operation mode of a probe according to the embodiment of the present disclosure.
Figure 3:
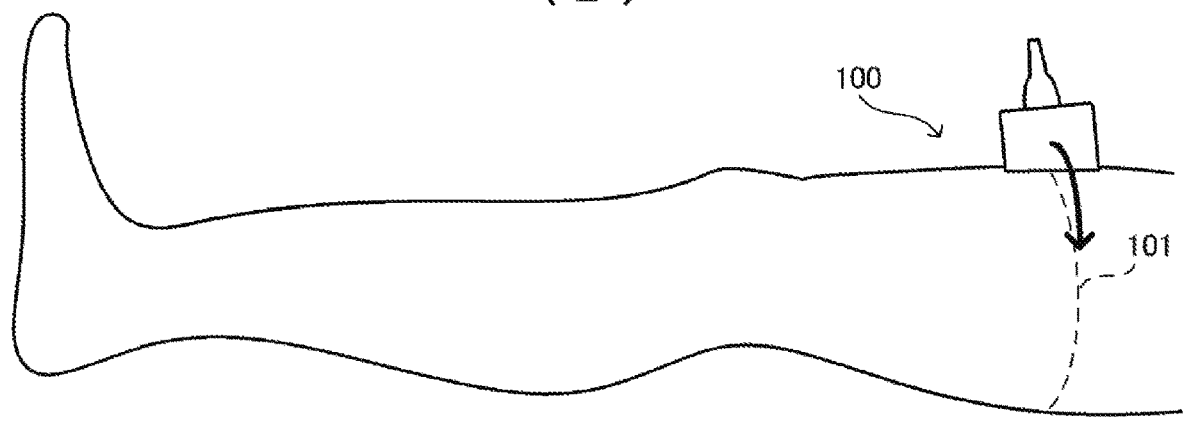

Here, an operation mode of the probe adapter 3 and the probe 2 is described by considering a case of imaging the cross section of the thigh in order to grasp the shape and muscle mass of the quadriceps (a thickness and muscle cross-sectional area of quadriceps) in the thigh as an example. FIG. 3(A) is a schematic diagram of the cross section of the thigh seen perpendicularly, and FIG. 3B is a schematic diagram of the thigh seen from the side.

A thigh 100 may have quadriceps 102 inside. The quadriceps 102 may be muscles extending from the vicinity of a knee joint to the vicinity of a hip joint at the front side of the thigh 100. In a case of imaging a cross section 101 of the thigh 100, first, gel 109 serving as an acoustic coupling material may be applied to a surface of the thigh 100 by the operator. Further, a suitable detachable-attaching part 36 corresponding to the shape of the surface of the thigh 100 may be selected and attached to the probe adapter 3.

In this state, the operator may bring the contact surface 33 of the probe adapter 3 attached to the probe 2 into contact with the surface of the thigh 100. Then, the operator may move the probe 2 and the probe adapter 3 along an outer circumference of the cross section 101 to be imaged.

Here, since the contact surface 33 may have the shape extending along the outer circumference of the cross section 101 of the thigh 100, a contact area between the contact surface 33 and the surface of the thigh 100 may be larger than a contact area between the ultrasonic wave transmitting-receiving surface 23 of the probe 2 and the surface of the thigh 100. Therefore, as illustrated in FIG. 3(A), when perpendicularly seeing the cross section 101, the operator may easily move the probe 2 in the state where the large contact area between the ultrasonic wave transmitting-receiving surface 23 and the surface of the thigh 100 is maintained while keeping the angle of the probe 2 substantially perpendicular to the outer circumference of the cross section 101. Further as illustrated in FIG. 3(B), when seeing the thigh 100 from one side, the operator may easily move the probe 2 while keeping the probe 2 in the tilted state at a certain angle with respect to the surface of the thigh 100.

Further, the image processing device 11 illustrated in FIG. 1 may include the transmission-reception processor 5, an image display unit 8, a controller 9, and the interface 10. The controller 9 may include a fragment image generating module 6 and an image composing module 7. The controller 9 may be comprised of a CPU and a memory. The fragment image generating module 6 and the image composing module 7 may be implemented as software by executing an ultrasonic wave imaging program installed in the memory (not illustrated) at the CPU.

The transmission-reception processor 5 may generate a transmission signal by providing a delay to a signal having a frequency within an ultrasonic wave range, and output it to the probe 2. By controlling the delay, the transmission-reception processor 5 may control an operating mode and a beam shape of the probe 2. Further, the transmission-reception processor 5 may receive a reception signal from the probe 2. The transmission-reception processor 5 may perform processing, such as analog-to-digital conversion on the inputted reception signal, and output the processed reception signal to the controller 9. While the probe 2 is moved along the surface of the thigh 100 as illustrated in FIGS. 3(A) and (B), the transmission-reception processor 5 may repeatedly output the transmission signal at a constant time interval, and every time the transmission signal is outputted, the transmission-reception processor 5 may acquire the reception signal of the ultrasonic wave received by the probe 2.

Based on the reception signal outputted by the transmission-reception processor 5, the fragment image generating module 6 may generate a fragment image which is a partial image of the imaging target, by executing image conversion processing according to the operating mode of the probe 2. While the probe 2 is moved along the surface of the thigh 100 as illustrated in FIGS. 3(A) and (B), the fragment image generating module 6 may generate a plurality of fragment images obtained by imaging the cross section 101 of the thigh 100 in various directions based on the reception signals repeatedly inputted from the transmission-reception processor 5, together with angle information.

The image composing module 7 may compose an image by partially superimposing the plurality of fragment images generated by the fragment image generating module 6. For example, the image composing module 7 may determine positions for superimposing the plurality of fragment images, by detecting feature amounts of the plurality of fragment images and finding a matching feature amount between areas included in the plurality of fragment images. Note that, here, the image composing module 7 may rotate the fragment images based on the detection angle obtained from the angle sensor 4 and perform the matching based on the rotated fragment images. Thus, the rotation angle of each fragment image may accurately be corrected and the positions for superimposing the plurality of fragment images may be determined more accurately.

The image display unit 8 may receive an image signal of the composed image by the image composing module 7 from the controller 9, and display the image.

When moving the probe 2 along the surface of the thigh 100 as illustrated in FIG. 3(B), a most-vivid (clearest) fragment image may be captured when the direction of the ultrasonic wave transmitted and received by the probe 2 is a given angular direction which is not perpendicular to the surface of the thigh 100 (e.g., a direction tilted by 3° to 10° from the perpendicular direction). Therefore, in the ultrasonic imaging apparatus 1, a plurality of vivid fragment images of the cross section 101 may be obtained in a state where the probe 2 is tilted in the given angular direction by the probe adapter 3, and the plurality of fragment images may be composed. Thus, the fragment images in which the cross section 101 is captured vividly may be obtained. Therefore, the image obtained by composing the plurality of fragment images may become an image in which the cross section 101 is captured vividly and over a wide range. Furthermore, by using the probe adapter 3, the fragment images may be generated without strongly pressing the probe 2 against the thigh 100, and therefore, the quadriceps 102 may be imaged in an accurate shape and not in a deformed state.

Next, the operating mode and the beam shape of the probe 2 are described.

Figure 4:
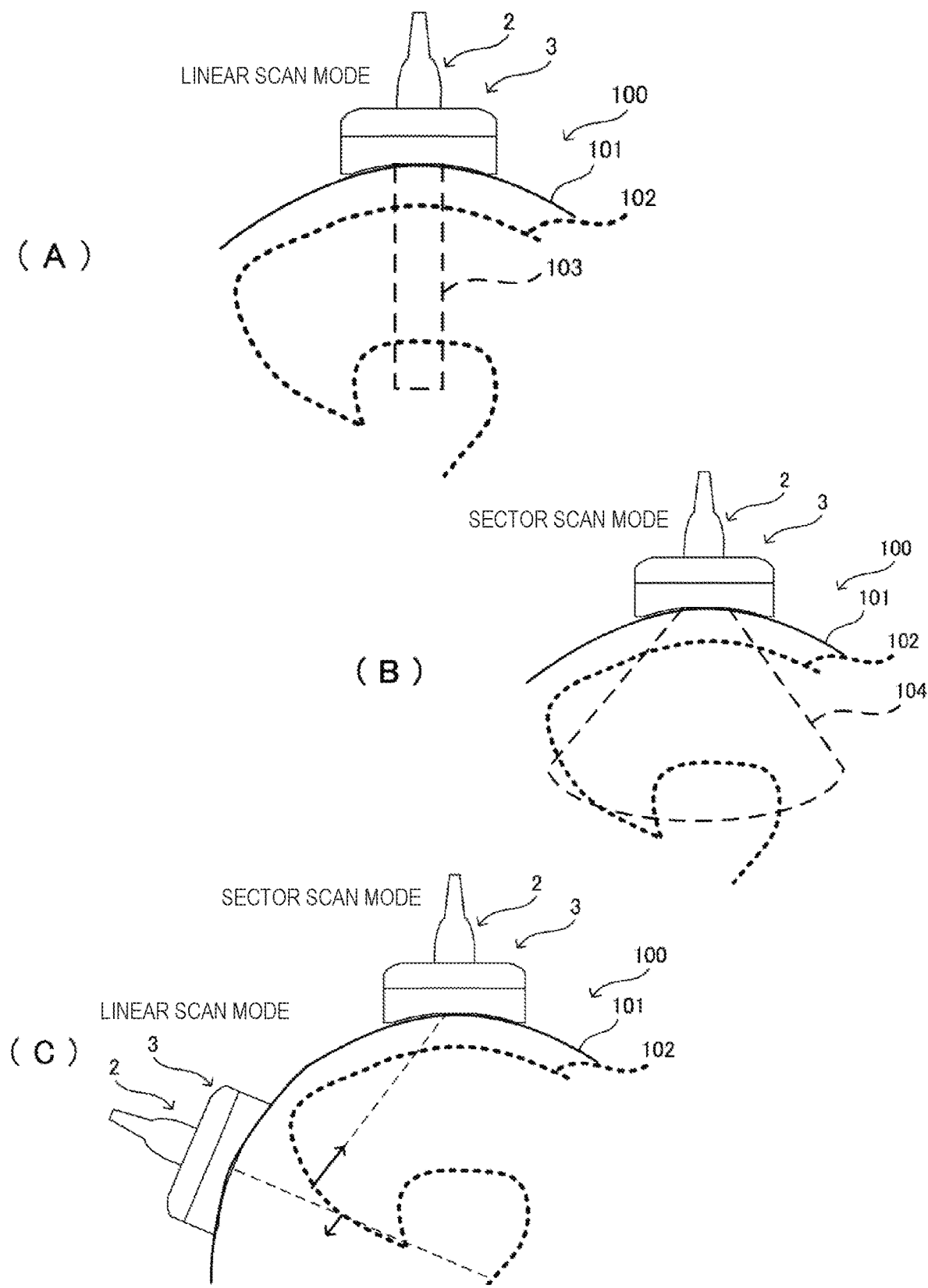
FIGS. 4(A) to 4(C) are views illustrating a control flow of the ultrasonic imaging apparatus according to the embodiment of the present disclosure.

The probe 2 may be operated in a linear scan mode. FIG. 4(A) is a view illustrating a case where the probe 2 operated in the linear scan mode images the cross section 101 of the thigh 100. When the probe 2 is operated in the linear scan mode, the transmission-reception processor 5 provided for the probe 2 may control the phases of the signals inputted and outputted by the respective ultrasonic oscillators 25 to be same so as to set the beam shape of the probe 2, so that the beam is oriented to a belt-shaped area 103 facing the ultrasonic wave transmission-reception surface 23. By operating the probe 2 in such a linear scan mode, the ultrasonic imaging apparatus 1 may generate the fragment image in which the belt-shaped area 103 is vividly captured. Note that, the linear scan mode may be achieved by a method different from the above-described method. For example, the transmission-reception processor 5 may sweep the oriented direction of the beam of the ultrasonic wave within the belt-shaped area 103, so that the fragment image in which the belt-shaped area 103 is vividly captured may be generated.

Further, the probe 2 may also be operated in a sector scan mode. FIG. 4(B) is a view illustrating a case where the probe 2 operated in the sector scan mode images the cross section 101 of the thigh 100. When the probe 2 is operated in the sector scan mode, the transmission-reception processor 5 may cause the signals inputted and outputted by the respective ultrasonic oscillators 25 to have a given difference in phase so as to set the beam shape of the probe 2, so that the beam is oriented to a fan-shaped area 104 centered on a direction orthogonal to the ultrasonic wave transmitting-receiving surface 23. By operating the probe 2 in such a sector scan mode, the ultrasonic imaging apparatus 1 may generate the fragment image in which the fan-shaped area 104 is vividly captured. Thus, when operating the probe in the sector scan mode, a wider angle range may be imaged compared to the case where the probe 2 is operated in the linear scan mode.

FIG. 4(C) is a view illustrating a difference in the internal tissue 102 which is imageable in the linear scan mode and the sector scan mode. In the linear scan mode, there may be a case where it is difficult to image a contour portion of the internal tissue (quadriceps) 102 under a specific condition. For example, in the linear scan mode, since the ultrasonic wave may be transmitted and received only in a direction orthogonal to the probe 2, if the contour portion of the internal tissue 102 extends parallel to the transmission-reception direction of the ultrasonic wave, that is, perpendicular to the surface of the thigh 100, it may be difficult for the ultrasonic wave to reach the contour portion, and a reflecting direction of the ultrasonic wave at the contour portion may easily become different from the transmission-reception direction of the ultrasonic wave. Therefore, in the linear scan mode, even in the vicinity of the probe 2, if the contour portion of the internal tissue extends perpendicular to the skin surface, it may be difficult to image the contour portion.

On the other hand, in the sector scan mode, since the ultrasonic wave may be transmitted and received within a fixed angle range centered on the direction orthogonal to the probe 2, even for the contour portion of the internal tissue 102 extending perpendicular to the skin surface, the ultrasonic wave may be transmitted and received to and from a non-parallel direction to the contour portion. Therefore, in the sector scan mode, even if the contour portion of the internal tissue 102 extends perpendicular to the skin surface, the contour portion may be imaged.

Thus, in this embodiment, an image may be obtained, in which not only the wide range of the cross section 101 is captured by composing only the plurality of fragment images using the linear scan mode of the ultrasonic imaging apparatus 1, but also the contour portion of the internal tissue 102 extending perpendicular to the skin surface is captured by composing the fragment images using the sector scan mode.

Figure 5:
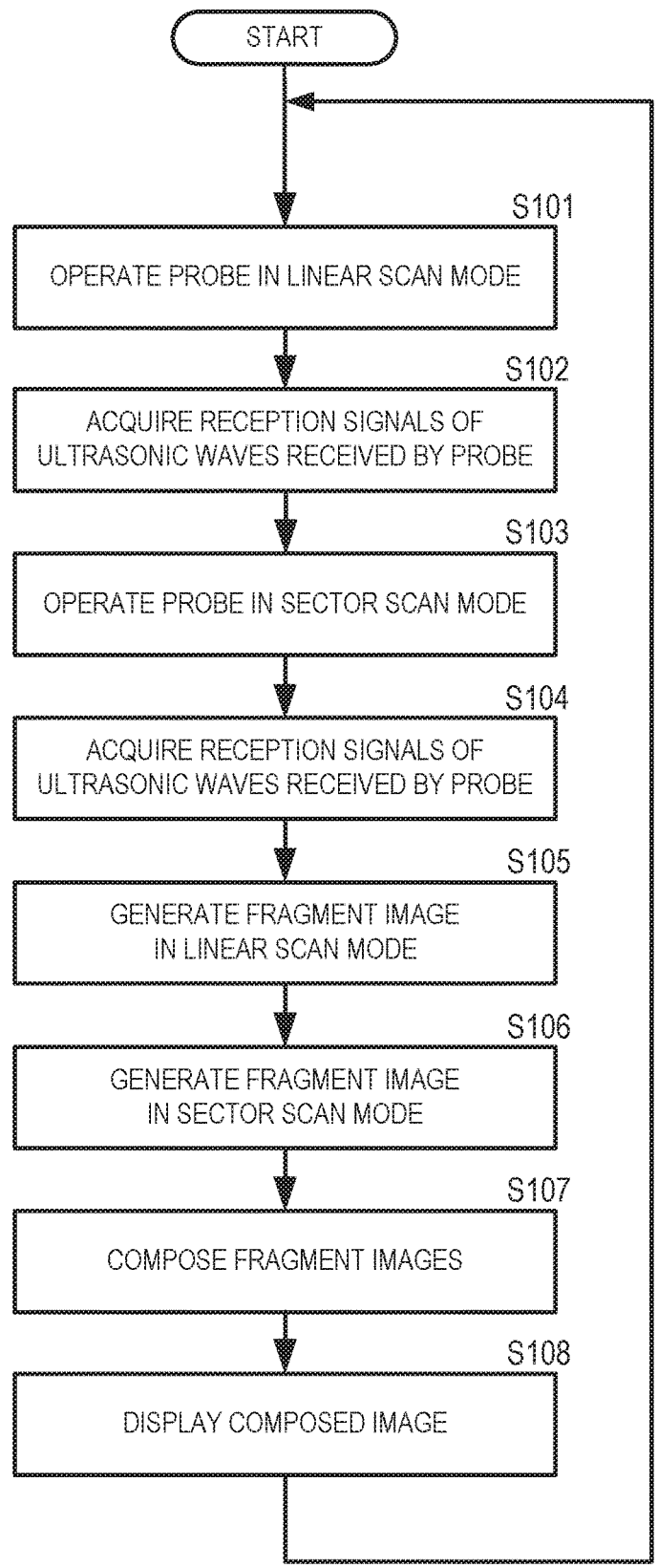
FIG. 5 is a flowchart illustrating a control flow of image composing processing of the ultrasonic imaging apparatus according to the embodiment of the present disclosure.

FIG. 5 is a flowchart illustrating a control flow of the ultrasonic imaging apparatus 1.

First, the ultrasonic imaging apparatus 1 may operate the probe 2 in the linear scan mode by the transmission-reception processor 5 (S101). Here, an operation frequency of the probe 2 may be set to about 6 MHz, for example. Thus, the probe 2 may transmit the ultrasonic waves in a belt-like beam shape perpendicularly from the skin surface. Further, the transmission-reception processor 5 may acquire the reception signals of the ultrasonic waves received by the probe 2 (S102).

In addition, immediately after operating the probe 2 in the linear scan mode, the transmission-reception processor 5 may operate the probe 2 in the sector scan mode in a state where the probe 2 is substantially at the same position (S103). The operation frequency of the probe here may be set to, for example, about 3 MHz, so that the ultrasonic waves reach farther away from the probe than in the linear scan mode. Thus, the probe 2 may transmit the ultrasonic waves in the fan-like beam shape centered on the vertical direction from the skin surface. Further, the transmission-reception processor 5 may acquire the reception signals of the ultrasonic waves received by the probe 2 (S104). Note that, the order of operating the probe 2 in the sector scan mode and operating the probe 2 in the linear scan mode may be reversed.

Figure 7:
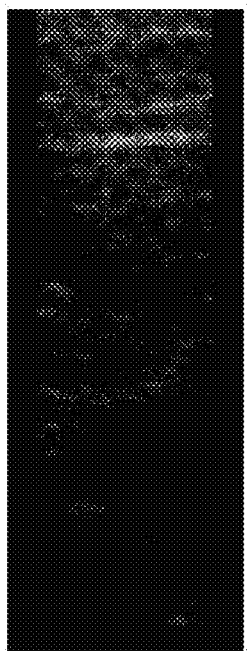
FIGS. 7(A) and 7(B) are views illustrating fragment images obtained in a linear scan mode and a sector scan mode, respectively.
Figure 7:
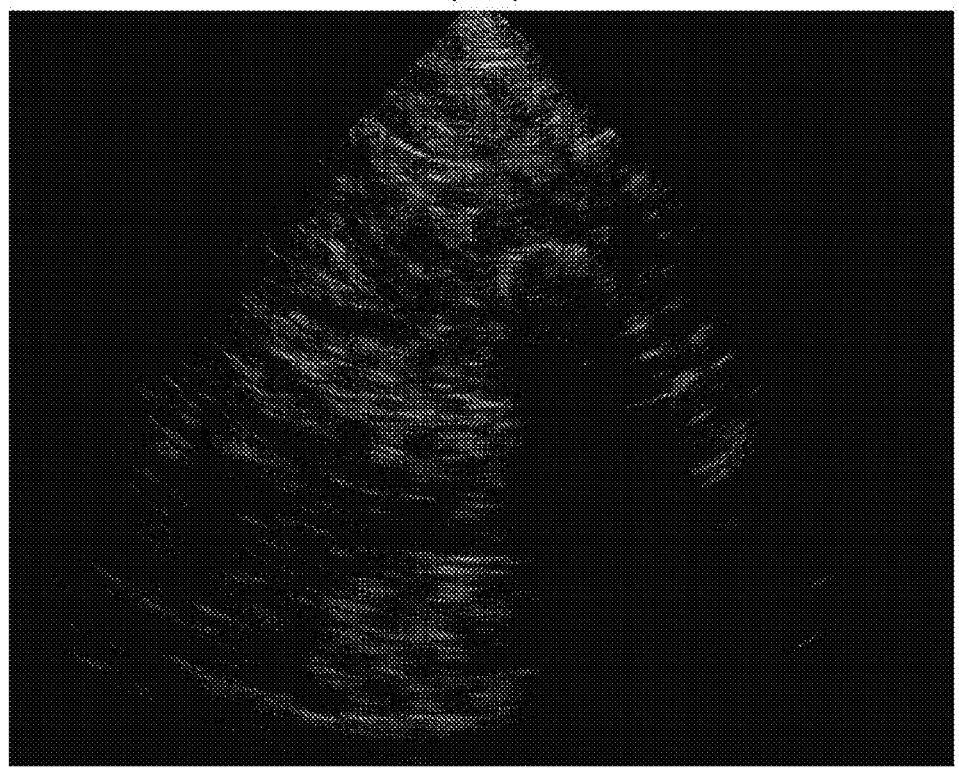

Next, the fragment image generating module 6 may generate the belt-shaped fragment image from the reception signal acquired in the linear scan mode (S105). FIG. 7(A) is a view illustrating the fragment image obtained in the linear scan mode. Further, the fragment image generating module 6 may generate the fan-shaped fragment image from the received signals acquired in the sector scan mode (S106). FIG. 7(B) is a view illustrating the fragment image obtained in the sector scan mode. When generating these fragment images, for example, a time axis of the reception signal may be converted into a position in the transmission direction of the ultrasonic wave and the amplitude (reflection intensity) of the reception signal may be converted into luminance information to generate the fragment images.

Next, the ultrasonic imaging apparatus 1 may compose, by the image composing module 7, the image in which the wide range of the cross-section 101 of the thigh 100 is captured, based on the fragment image in the linear scan mode and the fragment image in the sector scan mode generated in the previous processing (S107). Further, the ultrasonic imaging apparatus 1 may display the composed image on the image display unit 8 (S108).

The ultrasonic imaging apparatus 1 may repeat the control flow as described above at discrete time intervals, and update the image displayed on the image display unit 8. For example, the ultrasonic imaging apparatus 1 may repeat the control flow about 100 to 400 times while the operator moves the probe 2 about half the circumference of the thigh 100, so as to gradually expand the area of the cross section 101 displayed on the image display unit 8 and finally display the entire cross section 101 on the image display unit 8.

Figure 6:
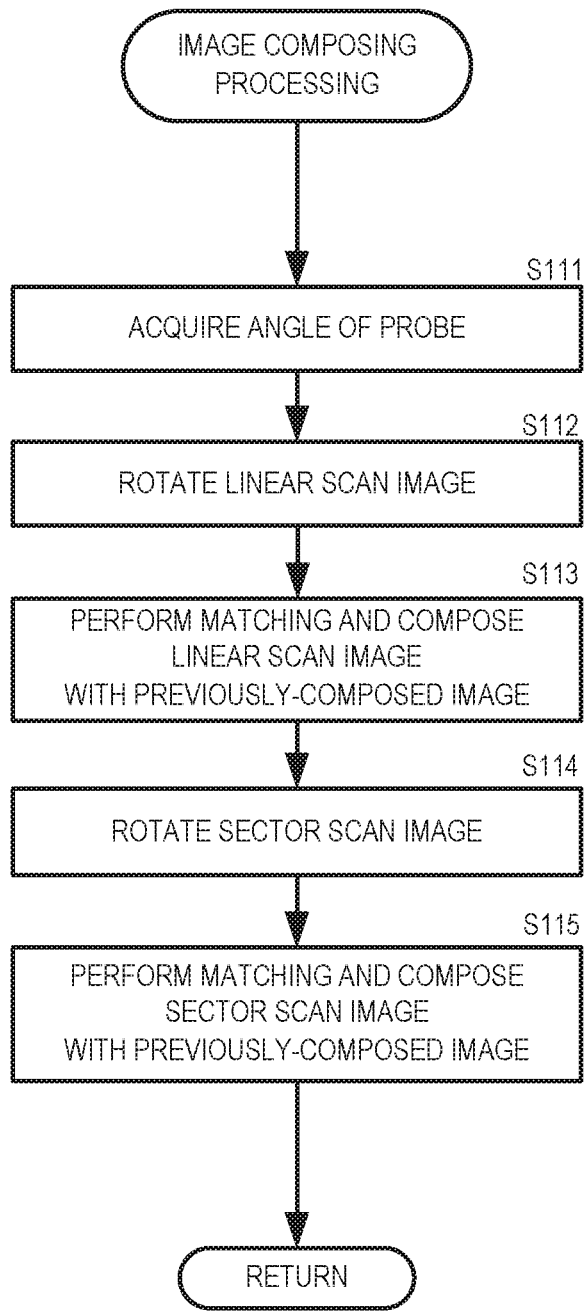
FIG. 6 is a flowchart illustrating scan modes of the ultrasonic imaging apparatus according to the embodiment of the present disclosure.

FIG. 6 is a flowchart illustrating a more detailed control flow of the image composing processing by the image composing module 7.

First, the image composing module 7 may acquire the output signal of the angle sensor 4 and acquire the tilted angle of the probe 2 from the vertical direction (S111). Next, the image composing module 7 may rotate the fragment image acquired from the fragment image generating module 6 in the linear scan mode, based on the tilted angle (S112).

Next, the image composing module 7 may acquire from the memory etc. the image obtained by the image composing processing executed previously, and compose the fragment image rotated in the processing described above, with the acquired image (S113). In this composing, the feature amounts (e.g., a luminance distribution) may be detected for every part included in the image composed previously and the rotated fragment image, a matching score between the feature amounts may be calculated to specify the position for superimposing the fragment image on the previously-composed image. Further, the luminance information of the fragment image may be overwritten at the specified position. Note that, the luminance information to overwrite may be obtained by a calculation etc. based on the luminance information of the previously-composed image and the luminance information of the fragment image.

Next, the image composing module 7 may rotate the fragment image obtained in the sector scan mode acquired from the fragment image generating module 6 based on the precedingly-acquired tilted angle (S114). Next, the image composing module 7 may compose the fragment image of the sector scan mode rotated in the above processing, on the image already composed with the fragment image of the linear scan mode (S115). This composing may also use matching of the feature amounts (e.g., luminance distribution) similarly to the composing processing described above. Note that, since the fragment image in the linear scan mode may have higher vividness in the vicinity of the probe than the fragment image in the sector scan mode, the composition may be performed, instead of composing all the fragment images obtained in the sector scan mode, only for a deep depth area where the vivid imaging is difficult in the linear scan mode or the contour portion extending perpendicular to the skin surface. Further, after this composing processing, image processing for emphasizing the contour portion of the internal tissue may be executed.

Figure 8:
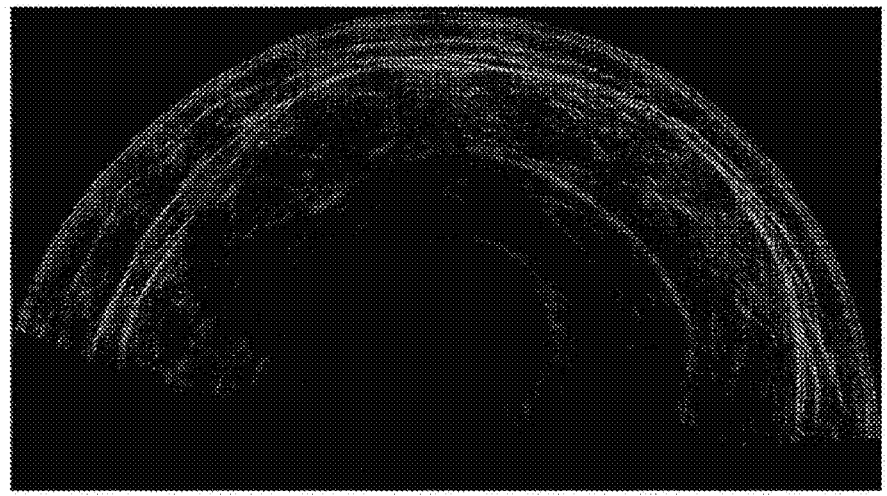
FIGS. 8(A) and 8(B) are views illustrating images obtained by composing a fragment image.
Figure 8:
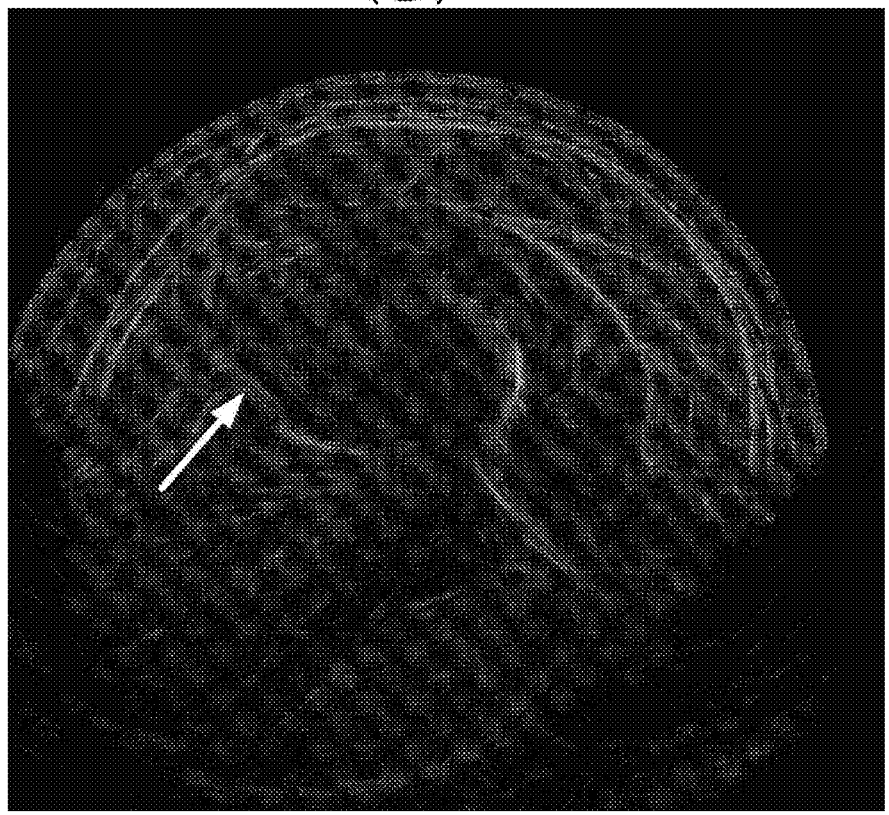

FIG. 8(A) is a view illustrating an image in a case where only the fragment image acquired in the linear scan mode is composed. FIG. 8(B) is a view illustrating an image obtained by composing the image illustrated in FIG. 8(A) with the fragment image acquired in the sector scan mode. In the image in the linear scan mode illustrated in FIG. 8(A), only the contour portion of the quadriceps parallel to the surface of the thigh 100 may be displayed, but in the image composed with the image in the sector scan mode illustrated in FIG. 8(B), in addition to the contour portion of the quadriceps parallel to the surface of the thigh 100, the contour portion of the quadriceps extending perpendicular to the surface of the thigh 100 may also be imaged vividly (arrow part).

By the above processing, the ultrasonic imaging apparatus 1 may image a wide range of the cross section of the object to be imaged using the ultrasonic wave, and the image in which the contour portion of the internal tissue (e.g., quadriceps) extending perpendicular to the outer circumference in the cross section of the object to be imaged is also vividly captured may be composed. Therefore, based on this image, the shape and thickness (muscle mass) of the internal tissue (e.g., quadriceps) of the object to be imaged may accurately be grasped.

Note that, although in the above embodiment the example in which the tilted angle of the fragment image detected by the angle sensor may be used for composing the fragment images in the image composing processing is described, the tilted angle of the fragment image may also be used in other processing. For example, instead of composing all the fragment images, a fragment image when the tilted angle changes over a certain angle may be extracted to only compose the extracted fragment image. In this manner, the number of times of composing the images may be reduced and a calculation cost and an image memory volume in the ultrasonic imaging apparatus may be lowered.

Further, although the example in which the matching of the feature amounts may be performed when composing the fragment image obtained in the linear scan mode and when composing the fragment image in the sector scan mode in the image composing processing described above is described, the result of the matching performed first may be used when performing the composing of the fragment image performed later, so as to determine the position for composing the fragment image.

Further, as the angle sensor described above, any sensor may be used as long as it is capable of calculating an angle from the detection value of the sensor by a calculation etc. For example, the angle of the probe may also be obtained by using an acceleration sensor.

Figure 9:
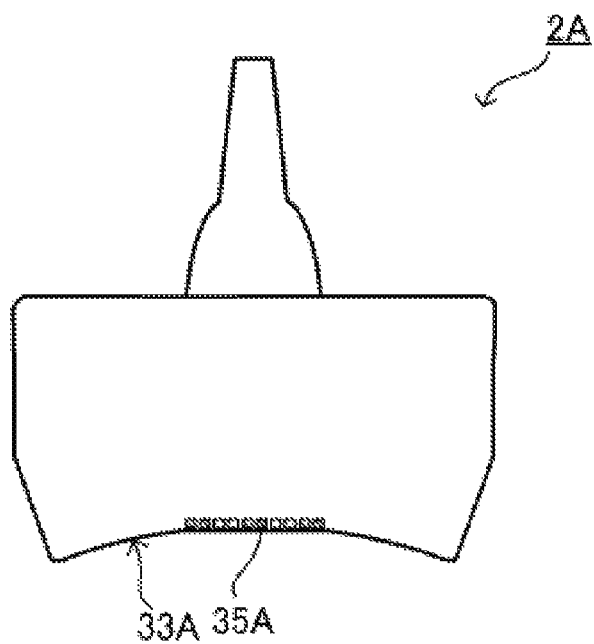
FIG. 9 is a structural view illustrating one modification of the probe according to the embodiment of the present disclosure.

Further, although in the ultrasonic imaging apparatus described above, the structural example in which the probe adapter may be attached to the probe is described, it may be structured by integrating the probe adapter with the probe. FIG. 9 is a view illustrating a structural example of the probe when the probe adapter is integrated therewith. The probe 2A illustrated in FIG. 9 may include a contact surface 33A and an ultrasonic wave transmitting-receiving surface 35A. The ultrasonic imaging apparatus of the present disclosure may also be structured using such a probe 2A.

Next, structural examples of a probe adapter according to embodiments are described.

Figure 10:
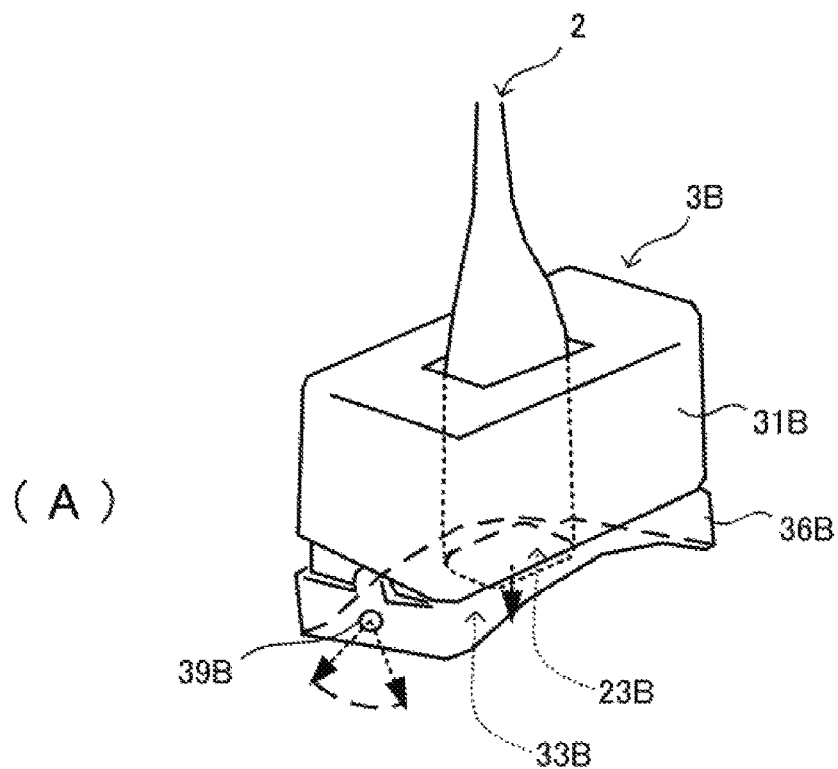
FIGS. 10(A) and 10(B) are structural views illustrating modifications of the probe adapter according to another embodiment of the present disclosure.
Figure 10:
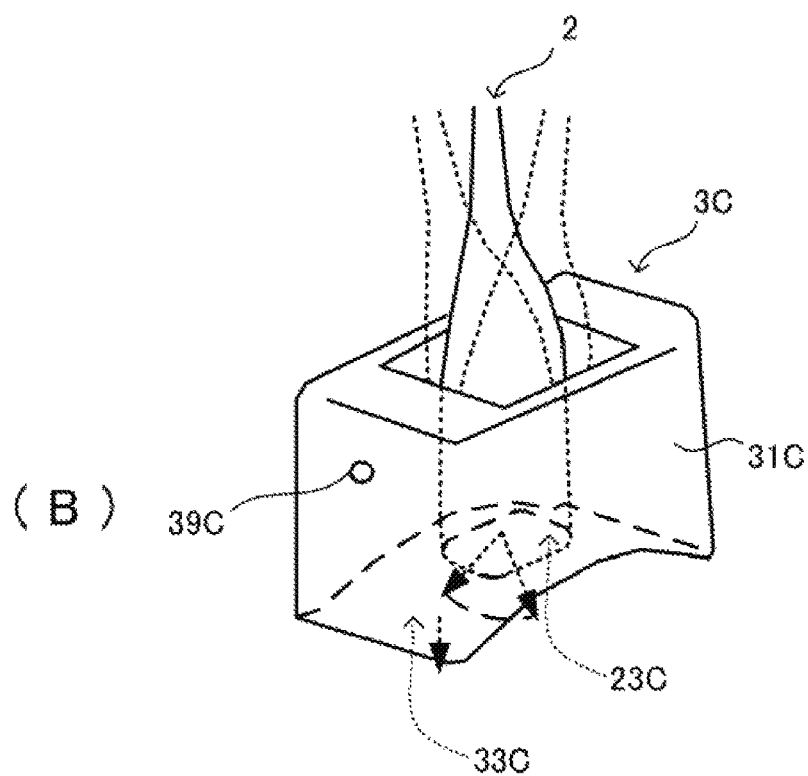

Although in the ultrasonic imaging apparatus described above, the detachable-attaching part which is detachable from the probe adapter may be provided so that the member constituting the contact surface is replaceable, without providing the detachable-attaching part, the facing direction of the contact surface may simply be variable. FIG. 10(A) is a view illustrating a structural example of a probe adapter 3B in a case where a facing direction of a contact surface 33B is variable.

The probe adapter 3B illustrated in FIG. 10(A) may include a housing 31B and an angle variable part 36B. The angle variable part 36B may be structured so that a lower face becomes the contact surface 33B having a shape extending along the outer circumference of the cross section of the object to be imaged, and the angle variable part 36B may be attached to a lower end part of the housing 31B. A shaft part 39B may be provided at a position where the angle variable part 36B is attached to the housing 31B. The shaft part 39B may be a part which pivotally supports the angle variable part 36B to the housing 31B, the angle variable part 36B may be rotatable with respect to the housing 31B by the shaft part 39B and also fixable thereto in a tilted state at a given angle.

More particularly, the contact surface 33B here may be formed into a substantially rectangular shape having a transverse direction and a longitudinal direction, and curve in the longitudinal direction. The shaft part 39B may pivotally support the angle variable part 36B to the housing 31B by having an axis in a direction substantially coinciding with the direction in which the contact surface 33B curves (longitudinal direction). Therefore, the angle variable part 36B may tilt about the shaft part 39B in the perpendicular direction (transverse direction) of the contact surface 33B to the direction in which the contact surface 33B curves (longitudinal direction).

Further, here, the shaft part 39B may be formed into a screw shape so as to be fitted into a screw hole formed in the housing 31B, so that the angle of the angle variable part 36B may be fixed by tightening the shaft part 39B, and the angle of the angle variable part 36B may be variable (rotatable) by loosening the shaft part 39B. Note that, a specific mechanism structured to fix the angle variable part 36B may not be limited to the screw mechanism as described above, and may be achieved by using other well-known mechanism, such as a latch mechanism.

By using the probe adapter 3B structured as described above, the facing direction of the contact surface 33B may be tilted from a facing direction of an ultrasonic wave transmitting-receiving surface 23B of the probe 2, and the tilted angle may be set being adjusted to arbitrary angle. Thus, when capturing the image of the cross section of the object to be imaged (e.g., the thigh) using this probe adapter 3B, by adjusting the angle of the contact surface 33B more finely, a more vivid fragment image or entire image may be obtained.

Note that, the angle between the contact surface 33B and the ultrasonic wave transmitting-receiving surface 23B may be adjusted by adjusting the angle itself of probe 2 attached to the probe adapter, other than adjusting the angle of the contact surface of the probe adapter. FIG. 10(B) is a view illustrating a structural example of a probe adapter 3C in a case where the angle itself at which the probe 2 is attached is adjustable.

The probe adapter 3C illustrated in FIG. 10(B) may include a housing 31C and a fixing part 39C. The housing 31C may be structured so that a lower surface becomes a contact surface 33C having a shape extending along the outer circumference of the cross section of the object to be imaged. This housing 31C may be structured to have extra space in an opening where the probe 2 is attached and by simply inserting the probe 2 into the opening, the probe 2 may be movable to an arbitrary angle. The fixing part 39C may be structured so that the probe 2 inserted into the opening is fixable at the arbitrary angle.

The fixing part 39C may be comprised of a clamp mechanism (not illustrated) provided in the housing 31C, a screw configured to tighten the clamp mechanism. Note that, the specific mechanism of the fixing part 39C may not be limited to the clamp mechanism as described above, and may be achieved by using other well-known mechanism, such as a latch mechanism.

By using the probe adapter 3C structured as described above, the angle of the probe 2 may arbitrarily be adjusted when attaching it to the probe adapter 3C, and a facing direction of the contact surface 33C of the probe adapter 3C and a facing direction of an ultrasonic wave transmitting-receiving surface 23C may be tilted at the arbitrary angle. Thus, also when capturing the image of the cross section of the object to be imaged (e.g., the thigh) using this probe adapter 3C, the angle between the ultrasonic wave transmitting-receiving surface 23C and the contact surface 33C may be adjusted more finely, a more vivid fragment image or entire image may be obtained.

Note that, here, although the structural examples in which the angle variable part or the fixing part may be provided to the probe adapter are described, instead of using the probe adapter, a structure may be adopted in which the angle variable part or the fixing part described above is provided to the probe itself so that the angle between the contact surface and the ultrasonic wave transmitting-receiving surface may be adjusted by the probe itself.

Next, a specific shape setting example of the contact surface is described.

Figure 11:
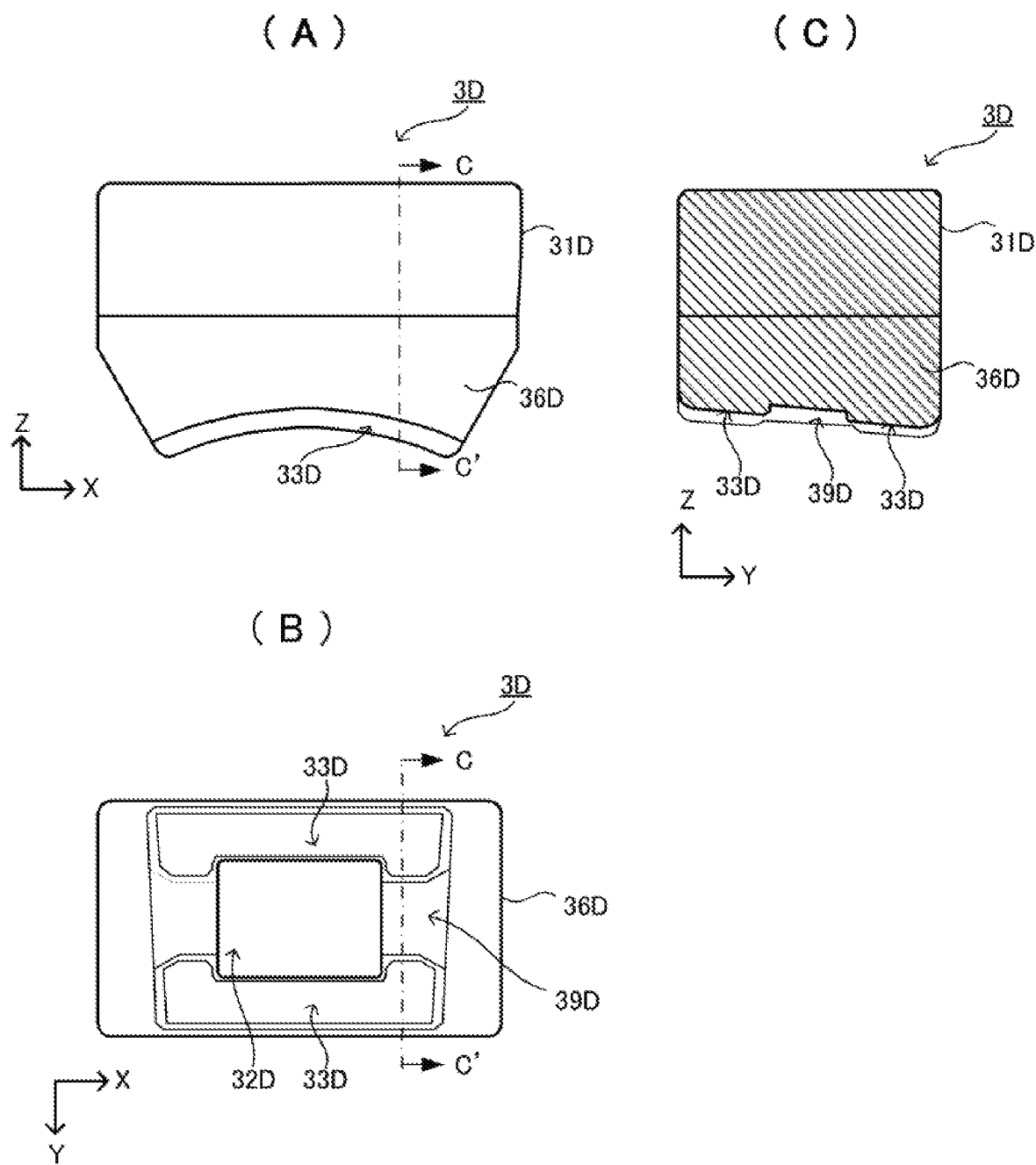
FIGS. 11(A) to 11(C) are structural views illustrating setting examples of a probe adapter according to another embodiment of the present disclosure.

FIG. 11(A) is a front elevational view of a probe adapter 3D. FIG. 11(B) is a plan view of the probe adapter 3D seen from the lower surface (contact surface) side. FIG. 11(C) is a cross-sectional view of the probe adapter 3D seen from a side-surface side.

The probe adapter 3D may include a housing 31D and a detachable-attaching part 36D. The housing 31D may be a member constituting an upper surface part of the probe adapter 3D. The detachable-attaching part 36D may be a member constituting a lower surface part of the probe adapter 3D and structured so that a lower surface becomes a contact surface 33D having a shape extending along the outer circumference of the cross section of the object to be imaged.

The contact surface 33D of the detachable-attaching part 36D may be formed with an opening 32D configured to expose the ultrasonic wave transmitting-receiving surface of the probe, and a groove portion 39D. The groove portion 39D may be formed to guide a suitable amount of the gel 109 illustrated in FIG. 3(A) to the periphery of the probe. Therefore, the groove portion 39D may be formed to extend in the direction in which the probe 2 is moved as illustrated in FIGS. 3(A) and (B), that is, in the direction in which the contact surface 33D curves and extends in FIG. 11(B) (longitudinal direction), and pass through the opening 32D.

By forming the groove portion 39D in the contact surface 33D as above, when moving the probe adapter 3D along the surface of the object to be imaged, the gel 109 may be prevented by the probe adapter 3D from being scraped off from the surface of the object to be imaged. Then, the gel 109 may be guided to the periphery of the probe along the groove portion 39D of the probe adapter 3D. Therefore, the cross section of the object to be imaged may be imaged in a suitable state via the gel 109.

Note that, in the probe adapter 3D, a corner portion declining from the contact surface 33D may be chamfered. Thus, it may be prevented that the corner portion of the probe adapter 3D comes into contact with the surface of the object to be imaged to scratch the surface of the object to be imaged or interrupt a smooth operation of the probe adapter 3D. In addition, both ends of the groove portion 39D of the probe adapter 3D are in particular widened, so that more gel 109 may be guided to the periphery of the probe.

By structuring the contact surface 33D of the probe adapter 3D in this manner, a suitable amount of the gel 109 may be kept around the tip end of the probe compared to the case where the cross section of the object to be imaged is imaged using only the probe. Therefore, it may become unnecessary for the operator to perform the imaging operation while paying attention to the amount of the gel 109, and the operability of the probe may be further enhanced.

The present disclosure may be implemented as described in each embodiment and each modification described above. However, the above description should be considered as illustrative in all respects and not restrictive. The scope of the present disclosure is indicated by the claims and not by the above-described embodiments. Furthermore, it is intended that the scope of the present disclosure includes meanings equivalent to the claims and all changes within the scope of the claims.

What is claimed is:

1. An ultrasonic imaging apparatus comprising:
a probe configured to be graspable and moveable by an operator; and
a probe adapter comprising:
a contact surface having a shape extending along an outer circumference of a cross section of an object to be imaged and a curved concave shape so as to substantially conform with a surface of the object to be imaged; and
a fixing portion configured to fix the probe having an ultrasonic wave transmitting-receiving surface at a given angle and expose the ultrasonic wave transmitting-receiving surface of the probe to a contact surface side when moving the probe along the outer circumference of the object to be imaged while the contact surface is in contact with the surface of the object to be imaged wherein a contact area between the contact surface of the probe adaptor and the surface of the object to be imaged is larger than a contact area between the ultrasonic wave transmitting-receiving surface of the probe and the surface of the object to be imaged, wherein the object to be imaged comprises a thigh, an upper arm, or an abdomen of a human body, and wherein the probe and the probe adapter are arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

2. The ultrasonic imaging apparatus of claim 1, wherein the contact surface is tilted from the ultrasonic wave transmitting-receiving surface of the probe fixed to the fixing portion.

3. The ultrasonic imaging apparatus of claim 1, wherein the probe adapter has a part on the contact surface side structured to be attachable thereto and detachable therefrom.

4. The ultrasonic imaging apparatus of claim 1, wherein the contact surface is structured to be rotatable on the surface of the object to be imaged.

5. The ultrasonic imaging apparatus of claim 1, wherein the ultrasonic wave transmitting-receiving surface is structured to be rotatable on the surface of the object to be imaged.

6. The ultrasonic imaging apparatus of claim 1 further comprising;
a transmission-reception processor configured to repeatedly transmit an ultrasonic wave into the object to be imaged from the probe and receive by the probe the ultrasonic wave reflected inside the object to be imaged every time the ultrasonic wave is transmitted; and
a fragment image generating module configured to generate a fragment image in which the object to be imaged is internally partially captured, based on the ultrasonic wave received by the probe.

7. An ultrasonic imaging apparatus, comprising:
a probe including a contact surface having a shape extending along an outer circumference of a cross section of an object to be imaged and having a curved concave shape so as to substantially conform with a surface of the object to be imaged, and an ultrasonic wave transmitting-receiving surface exposed to a contact surface side when moving the probe along the outer circumference of the object to be imaged while the contact surface is in contact with the surface of the object to be imaged wherein a contact area between the contact surface of the probe and the surface of the object to be imaged is larger than a contact area between the ultrasonic wave transmitting-receiving surface of the probe and the surface of the object to be imaged;

a transmission-reception processor configured to repeatedly transmit an ultrasonic wave into the object to be imaged from the probe and receive by the probe the ultrasonic wave reflected inside the object to be imaged every time the ultrasonic wave is transmitted; and a fragment image generating module configured to generate a fragment image in which the object to be imaged is internally partially captured, based on the ultrasonic wave received by the probe, wherein the object to be imaged comprises a thigh, an upper arm, or an abdomen of a human body, and wherein the probe is arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

8. The ultrasonic imaging apparatus of claim 6, further comprising an image composing module configured to compose a plurality of fragment images generated by the fragment image generating module.

9. The ultrasonic imaging apparatus of claim 8, wherein the transmission-reception processor repeatedly switches an operating state of the probe between a state where the probe is operated in a linear scan mode in which a range extending in a belt shape from the ultrasonic wave transmitting-receiving surface is imaged, and a state where the probe is operated in a sector scan mode in which a range spreading in a fan shape from the ultrasonic wave transmitting-receiving surface is imaged.

10. The ultrasonic imaging apparatus of claim 8, further comprising an angle sensor configured to detect a direction in which the ultrasonic wave transmitting-receiving surface faces, wherein the image composing module composes an image in which the plurality of fragment images are partially superimposed on each other, based on an angle detected by the angle sensor.

11. The ultrasonic imaging apparatus of claim 8, wherein the image composing module composes an image in which the plurality of fragment images are partially superimposed on each other, based on matching of parts included in the plurality of fragment images.

12. An ultrasonic imaging method, comprising:

repeatedly transmitting, from a probe that is fixed to a probe adapter including a contact surface having a shape extending along an outer circumference of a cross section of an object to be imaged and a curved concave shape so as to substantially conform with a surface of the object to be imaged, and a fixing portion configured to fix the probe having an ultrasonic wave transmitting-receiving surface and expose the ultrasonic wave transmitting-receiving surface of the probe to a contact surface side when moving the probe along the outer circumference of the object to be imaged while the contact surface is in contact with the surface of the object to be imaged wherein a contact area between the contact surface of the probe adaptor and the surface of the object to be imaged is larger than a contact area between the ultrasonic wave transmitting-receiving surface of the probe and the surface of the object to be imaged, an ultrasonic wave into the object to be imaged and receiving by the probe the ultrasonic wave reflected inside the object to be imaged every time the ultrasonic wave is transmitted;

generating a fragment image in which the object to be imaged is internally partially captured, based on the ultrasonic wave received by the repeated-transmission and reception of the ultrasonic wave; and composing a plurality of fragment images generated by the fragment image generation, wherein the object to be imaged comprises a thigh, an upper arm, or an abdomen of a human body, and wherein the probe and the probe adapter are arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

13. An ultrasonic imaging method, comprising:

repeatedly transmitting, from a probe including a contact surface having a shape extending along an outer circumference of a cross section of an object to be imaged and a curved concave shape so as to substantially conform with a surface of the object to be imaged, and an ultrasonic wave transmitting-receiving surface exposed to a contact surface side when moving the probe along the outer circumference of the object to be imaged while the contact surface is in contact with the surface of the object to be imaged wherein a contact area between the contact surface of the probe adaptor and the surface of the object to be imaged is larger than a contact area between the ultrasonic wave transmitting-receiving surface of the probe and the surface of the object to be imaged, an ultrasonic wave into the object to be imaged and receiving by the probe the ultrasonic wave reflected inside the object to be imaged every time the ultrasonic wave is transmitted;

generating a fragment image in which the object to be imaged is internally partially captured, based on the ultrasonic wave received by the repeated-transmission and reception of the ultrasonic wave; and composing a plurality of fragment images generated by the fragment image generation, wherein the object to be imaged comprises a thigh, an upper arm, or an abdomen of a human body, and wherein the probe is arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

14. An ultrasonic imaging program, causing a computer to execute processing of imaging an inside of an object to be imaged, by an ultrasonic wave obtained by the ultrasonic wave being transmitted to the object to be imaged and reflecting inside the object to be imaged, comprising causing the computer to:

repeatedly transmit, from a probe that is fixed to a probe adapter including a contact surface having a shape extending along an outer circumference of a cross section of the object to be imaged and a curved concave shape so as to substantially conform with a surface of the object to be imaged, and a fixing portion configured to fix the probe having an ultrasonic wave transmitting-receiving surface and expose the ultrasonic wave transmitting-receiving surface of the probe to a contact surface side when moving the probe along the outer circumference of the object to be imaged while the contact surface is in contact with the surface of the object to be imaged wherein a contact area between the contact surface of the probe adaptor and the surface of the object to be imaged is larger than a contact area between the ultrasonic wave transmitting-receiving surface of the probe and the surface of the object to be imaged, an ultrasonic wave into the object to be imaged and receive by the probe the ultrasonic wave reflected inside the object to be imaged every time the ultrasonic wave is transmitted;

generate a fragment image in which the object to be imaged is internally partially captured based on the ultrasonic wave received by the repeated-transmission and reception of the ultrasonic wave; and compose a plurality of fragment images generated by the fragment image generation, wherein the object to be imaged comprises a thigh, an upper arm, or an abdomen of a human body, and wherein the probe and the probe adapter are arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

15. An ultrasonic imaging program, causing a computer to execute processing of imaging an inside of an object to be imaged, by an ultrasonic wave obtained by the ultrasonic wave being transmitted to the object to be imaged and reflecting inside the object to be imaged, comprising causing the computer to:

repeatedly transmit, from a probe including a contact surface having a shape extending along an outer circumference of a cross section of the object to be imaged and a curved concave shape so as to substantially conform with a surface of the object to be imaged, and an ultrasonic wave transmitting-receiving surface exposed to a contact surface side when moving the probe along the outer circumference of the object to be imaged while the contact surface is in contact with the surface of the object to be imaged wherein a contact area between the contact surface of the probe adaptor and the surface of the object to be imaged is larger than a contact area between the ultrasonic wave transmitting-receiving surface of the probe and the surface of the object to be imaged, an ultrasonic wave into the object to be imaged and receive by the probe the ultrasonic wave reflected inside the object to be imaged every time the ultrasonic wave is transmitted;

generate a fragment image in which the object to be imaged is internally partially captured, based on the ultrasonic wave received by the repeated-transmission and reception of the ultrasonic wave; and compose a plurality of fragment images generated by the fragment image generation, wherein the object to be imaged comprises a thigh, an upper arm, or an abdomen of a human body, and wherein the probe is arranged to be moved along the outer circumference of the cross section of the object to be imaged while exposing the ultrasonic wave transmitting-receiving surface of the probe to the contact surface side and keeping the angle of the probe substantially perpendicular to the outer circumference of the cross section of the object to be imaged.

16. The ultrasonic imaging apparatus of claim 9, further comprising an angle sensor configured to detect a direction in which the ultrasonic wave transmitting-receiving surface faces, wherein the image composing module composes an image in which the plurality of fragment images are partially superimposed on each other, based on the angle detected by the angle sensor.

17. The ultrasonic imaging apparatus of claim 9, wherein the image composing module composes an image in which the plurality of fragment images are partially superimposed on each other, based on matching of parts included in the plurality of fragment images.

18. The ultrasonic imaging apparatus of claim 10, wherein the image composing module composes an image in which the plurality of fragment images are partially superimposed on each other, based on matching of parts included in the plurality of fragment images.

* * * * *

UNITED STATES PATENT AND TRADEMARK OFFICE
CERTIFICATE OF CORRECTION

| | |
|---|---|
| PATENT NO. | : 11,147,534 B2 |
| APPLICATION NO. | : 15/744729 |
| DATED | : October 19, 2021 |
| INVENTOR(S) | : Arai et al. |

Page 1 of 1

It is certified that error appears in the above-identified patent and that said Letters Patent is hereby corrected as shown below:

In the Specification

In Column 1, Line 66, delete "[Patent Document 2]" and insert --[Patent Document 3]--.

In the Claims

In Column 16, Line 37, Claim 13, delete "probe adaptor" and insert --probe--.

In Column 18, Line 5, Claim 15, delete "probe adaptor" and insert --probe--.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*